(12) United States Patent
Borchardt et al.

(10) Patent No.: US 7,947,843 B2
(45) Date of Patent: May 24, 2011

(54) CRYSTALLINE CHEMOTHERAPEUTIC

(75) Inventors: Thomas B. Borchardt, Kenosha, WI (US); Michael J. Rozema, Kenosha, WI (US); Shailendra V. Bordawekar, Gurnee, IL (US); Alexander F. Chu-Kung, Highland Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 129 days.

(21) Appl. No.: 12/251,879

(22) Filed: Oct. 15, 2008

(65) Prior Publication Data

US 2009/0118344 A1    May 7, 2009

Related U.S. Application Data

(60) Provisional application No. 60/981,236, filed on Oct. 19, 2007.

(51) Int. Cl.
*C07D 231/56* (2006.01)
(52) U.S. Cl. .................................. 548/362.1
(58) Field of Classification Search ............... 514/407; 548/362.1
See application file for complete search history.

(56) References Cited

U.S. PATENT DOCUMENTS 7,297,709 B2    11/2007   Dai et al.
2005/0020603 A1*    1/2005   Dai et al. .................. 514/252.06

FOREIGN PATENT DOCUMENTS

WO    WO2004113304 A1    12/2004
WO    WO2007050574 A1    5/2007

OTHER PUBLICATIONS

U.S. Pharmacopoeia, pp. 1843-1884 (1995).
Dai, et al, "Discover of N-(4-(3-Amino-1H-indazol-4-yl)phenyl)-N'-(2-fluoro-5-methylphenyl)urea (ABT-869), a 3-Aminoindazole-Based Orally Active Multitargeted Receptor Tyrosine Kinase Inhibitor", J. Med. Chem., 50, 1584-1597 (2007).
International Search Report, Jan. 16, 2009.
Aulton M.E. ed., Pharmaceutics: The Science of Dosage Form Design, 2nd Edition, Churchill Livingstone, 2004, Table of Contents.
Hilfiker R., ed., Polymorphism in the Pharmaceutical Industry, Wiley-VCH Verlag GmbH & Co., KGaA, Weinheim, Germany, 2006, Table of Contents.
Morris K.M., "Structural Aspects of Hydrate and Solvates," Polymorphism in Pharmaceutical Solids, 1999, pp. 125-181.
Spanish Minerals: X-rays and the Diffraction by Crystals, http://translate.googleusercontent.com/translate_c?hl=en&sl=es&u=http://www.spanishmi, (2010).

* cited by examiner

*Primary Examiner* — Yong Chu
(74) *Attorney, Agent, or Firm* — Glen Gesicki

(57) ABSTRACT

N-[4-(3-Amino-1H-indazol-4-yl)phenyl]-N'-(2-fluoro-5-methylphenyl)urea Hydrate Crystalline Form 1, ways to make it, formulations comprising it and made with it and methods of treating patients having disease using it are disclosed.

1 Claim, 1 Drawing Sheet

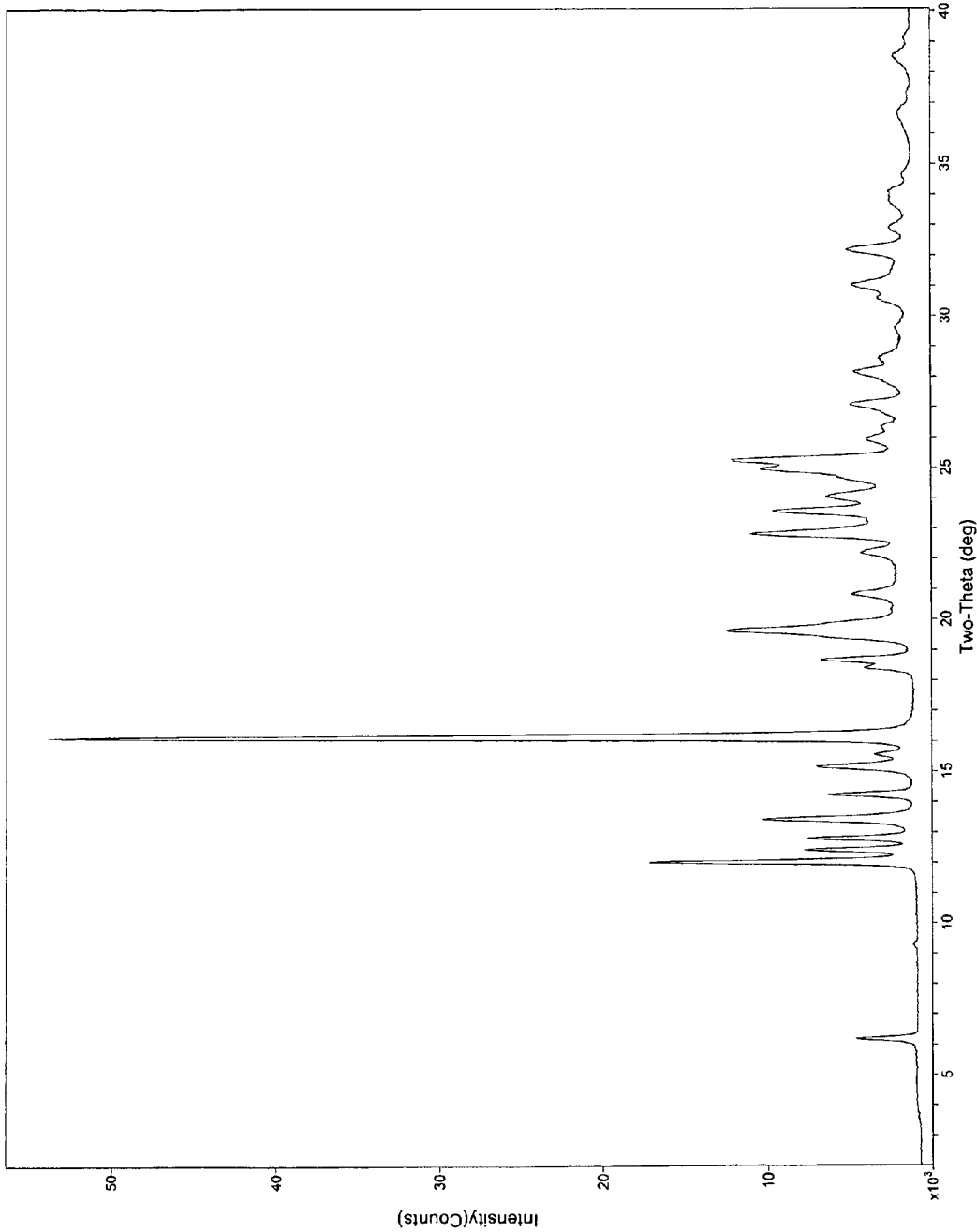

CRYSTALLINE CHEMOTHERAPEUTIC

CROSS-REFERENCE TO RELATED APPLICATIONS

This application claims priority to U.S. Provisional Application No. 60/981,236, filed Oct. 19, 2007 and hereby incorporated in its entirety by reference.

FIELD OF THE INVENTION

This invention pertains to N-[4-(3-Amino-1H-indazol-4-yl)phenyl]-N'-(2-fluoro-5-methylphenyl)urea Hydrate Crystalline Form 1, ways to make it, formulations comprising it and made with it and methods of treating patients having disease using it.

BACKGROUND OF THE INVENTION

N-[4-(3-Amino-1H-indazol-4-yl)phenyl]-N'-(2-fluoro-5-methylphenyl)urea (ABT-869) belongs to a family of protein tyrosine kinases (PTKs) which catalyze the phosphorylation of specific tyrosine residues in cellular proteins. Aberrant or excessive PTK activity has been observed in many disease states including benign and malignant proliferative disorders and diseases resulting from inappropriate activation of the immune system.

Crystallinity of hydrates of ABT-869 may effect, among other physical and mechanical properties, their stability, solubility, dissolution rate, hardness, compressibility and melting point. Because ease of manufacture and formulation of ABT-869 is dependent on some, if not all, of these properties, there is an existing need in the chemical and therapeutic arts for identification of crystalline forms of ABT-869 and ways to reproducibly make them.

SUMMARY OF THE INVENTION

One embodiment of this invention, therefore, pertains to N-[4-(3-Amino-1H-indazol-4-yl)phenyl]-N'-(2-fluoro-5-methylphenyl)urea Hydrate Crystalline Form 1 which, when measured at about 25° C. with radiation at 1.54178 Å, is characterized by a powder diffraction pattern having respective 2θ values of about 6.2°, 12.0°, 12.4°, 12.8°, 13.4°, 14.2°, 15.2°, 15.6°, 16.2° and 19.7°.

Another embodiment pertains to formulations comprising an excipient and N-[4-(3-Amino-1H-indazol-4-yl)phenyl]-N'-(2-fluoro-5-methylphenyl)urea Hydrate Crystalline Form 1 which, when measured at about 25° C. with radiation at 1.54178 Å, is characterized by a powder diffraction pattern having respective 2θ values of about 6.2°, 12.0°, 12.4°, 12.8°, 13.4°, 14.2°, 15.2°, 15.6°, 16.2° and 19.7°.

Still another embodiment pertains to methods of treating cancer in a mammal comprising administering thereto, with or without one or more than one additional anticancer drugs, a therapeutically effective amount of N-[4-(3-Amino-1H-indazol-4-yl)phenyl]-N'-(2-fluoro-5-methylphenyl)urea Hydrate Crystalline Form 1 which, when measured at about 25° C. with radiation at 1.54178 Å, is characterized by a powder diffraction pattern having respective 2θ values of about 6.2°, 12.0°, 12.4°, 12.8°, 13.4°, 14.2°, 15.2°, 15.6°, 16.2° and 19.7°.

Still another embodiment pertains to a process for making N-[4-(3-Amino-1H-indazol-4-yl)phenyl]-N'-(2-fluoro-5-methylphenyl)urea Hydrate Crystalline Form 1 comprising:
making N-[4-(3-amino-1H-indazol-4-yl)phenyl]-N'-(2-fluoro-5-methylphenyl)urea;

providing a mixture comprising N-[4-(3-amino-1H-indazol-4-yl)phenyl]-N'-(2-fluoro-5-methylphenyl)urea and solvent, wherein the N-[4-(3-amino-1H-indazol-4-yl)phenyl]-N'-(2-fluoro-5-methylphenyl)urea is completely dissolved in the solvent;

causing N-[4-(3-Amino-1H-indazol-4-yl)phenyl]-N'-(2-fluoro-5-methylphenyl)urea Hydrate Crystalline Form 1 to exist in the mixture, which N-[4-(3-Amino-1H-indazol-4-yl) phenyl]-N'-(2-fluoro-5-methylphenyl)urea Hydrate Crystalline Form 1, when measured at about 25° C. with radiation at 1.54178 Å, is characterized by a powder diffraction pattern having respective 2θ values of about 6.2°, 12.0°, 12.4°, 12.8°, 13.4°, 14.2°, 15.2°, 15.6°, 16.2° and 19.7°; and isolating the N-[4-(3-Amino-1H-indazol-4-yl)phenyl]-N'-(2-fluoro-5-methylphenyl)urea Hydrate Crystalline Form 1.

Still another embodiment comprises N-[4-(3-Amino-1H-indazol-4-yl)phenyl]-N'-(2-fluoro-5-methylphenyl)urea Hydrate Crystalline Form 1 prepared by the process of the preceeding embodiment.

In a process for making N-[4-(3-Amino-1H-indazol-4-yl) phenyl]-N'-(2-fluoro-5-methylphenyl)urea Hydrate Crystalline Form 1 comprising reacting an acid or diacid salt of N-[4-(3-amino-1H-indazol-4-yl)phenyl]-N'-(2-fluoro-5-methylphenyl)urea and a base and crystallizing or recrystallizing the N-[4-(3-Amino-1H-indazol-4-yl)phenyl]-N'-(2-fluoro-5-methylphenyl)urea Hydrate Crystalline Form 1, still another embodiment of this invention comprises crystallizing or recrystallizing the N-[4-(3-Amino-1H-indazol-4-yl)phenyl]-N'-(2-fluoro-5-methylphenyl)urea Hydrate Crystalline Form 1 from a solid, semisolid, wax or oil form of N-[4-(3-amino-1H-indazol-4-yl)phenyl]-N'-(2-fluoro-5-methylphenyl)urea that is mixed with one or more than one solvent from the deprotonation reaction.

Still another embodiment comprises N-[4-(3-amino-1H-indazol-4-yl)phenyl]-N'-(2-fluoro-5-methylphenyl)urea Hydrate Crystalline Form 1 prepared by the process of the preceeding embodiment.

Still another embodiment comprises ABT-869 for use in preparing N-[4-(3-Amino-1H-indazol-4-yl)phenyl]-N'-(2-fluoro-5-methylphenyl)urea Hydrate Crystalline Form 1.

Still another embodiment comprises a salt of ABT-869 for use in preparing N-[4-(3-Amino-1H-indazol-4-yl)phenyl]-N'-(2-fluoro-5-methylphenyl)urea Hydrate Crystalline Form 1.

Still another embodiment comprises the hydrochloride salt of ABT-869 for use in preparing N-[4-(3-Amino-1H-indazol-4-yl)phenyl]-N'-(2-fluoro-5-methylphenyl)urea Hydrate Crystalline Form 1.

Still another embodiment comprises ABT-869.¼ Ethanolate Crystalline Form 1 for use in preparing N-[4-(3-amino-1H-indazol-4-yl)phenyl]-N'-(2-fluoro-5-methylphenyl) urea-Hydrate Crystalline Form 1.

BRIEF DESCRIPTION OF THE FIGURES

FIG. 1 is a powder x-ray diffraction pattern of N-[4-(3-amino-1H-indazol-4-yl)phenyl]-N'-(2-fluoro-5-methylphenyl)urea Hydrate Crystalline Form 1.

DETAILED DESCRIPTION OF THE INVENTION

This invention pertains to discovery of N-[4-(3-amino-1H-indazol-4-yl)phenyl]-N'-(2-fluoro-5-methylphenyl)urea Hydrate Crystalline Form 1, ways to make it, ways to characterize it, formulations containing it and made with it, and methods of treating cancer using it. The terms "N-[4-(3- amino-1H-indazol-4-yl)phenyl]-N'-(2-fluoro-5-methylphenyl)urea" and "ABT-869" are meant to be used interchangeably. The term "hydrate" means having water associated therewith.

The terms "ABT-869" and "an ABT-869" without any indicia of crystallinity or non-crystallinity associated with it, as used herein, mean amorphous ABT-869, a crystalline ABT-869, microcrystalline ABT-869, ABT-869 in solution, a semisolid, wax or oil form of ABT-869, mixtures thereof and the like.

The terms "crystalline" and "microcrystalline," as used herein, mean having a regularly repeating arrangement of molecules which is maintained over a long range or external face planes.

Unless stated otherwise, percentages herein are weight/weight (w/w) percentages.

The term "hydrochloride salt," as used herein, means having associated therewith one or more than one hydrochloride equivalent.

The term "solvent," as used herein, means a liquid in which a compound is soluble or partially soluble enough at a given concentration to dissolve or partially dissolve the compound.

The term "anti-solvent," as used herein, means a liquid in which a compound is insoluble enough at a given concentration to be effective for precipitating that compound from a solution.

Solvents and anti-solvents may be mixed with or without separation of phases.

The term "monohydrate" means having associated therewith one water molecule and can be represented by ".$H_2O$"

It is meant to be understood that, because many solvents and anti-solvents contain impurities, the level of impurities in solvents and anti-solvents for the practice of this invention, if present, are at a low enough concentration that they do not interfere with the intended use of the solvent in which they are present.

The term "acid," as used herein, means a compound having at least one acidic proton. Examples of acids for the practice of this invention include, but are not limited to, hydrochloric acid, hydrobromic acid, trifluoroacetic acid, trichloroacetic acid, sulfuric acid, phosphoric acid and the like.

The term "base," as used herein, means a compound capable of accepting a proton. Examples of bases for the practice of this invention include, but are not limited to, sodium carbonate, sodium bicarbonate, potassium carbonate, potassium bicarbonate, dibasic sodium phosphate (i.e. $Na_2HPO_4$, $K_2HPO_4$ and the like), triethylamine, diisopropylethylamine and the like.

Causing ABT-869 Hydrate Crystalline Form 1 to exist in a mixture comprising water, ABT-869 and solvent, wherein the ABT-869 has completely dissolved, is known as nucleation.

For the practice of this invention, nucleation may be made to occur by means such as solvent removal, temperature change, solvent-miscible anti-solvent addition, solvent-immiscible anti-solvent addition, chafing or scratching the interior of the container, preferably a glass container, in which nucleation is meant to occur with an implement such as a glass rod or a glass bead or beads, or a combination of the foregoing.

For the practice of this invention, nucleation may be followed by crystal growth, accompanied by crystal growth, or followed and accompanied by crystal growth during which, and as a result of which, the percentage of ABT-869 Hydrate Crystalline Form 1 increases.

The term "isolating" as used herein, means separating ABT-869 Hydrate Crystalline Form 1 from solvent, anti-solvent, or a mixture of solvent anti-solvent. This is typically accomplished by means such as centrifugation, filtration with or without vacuum, filtration with positive pressure, distillation, evaporation or a combination thereof.

Therapeutically acceptable amounts of ABT-869 Hydrate Crystalline Form 1 depend on recipient of treatment, disorder being treated and severity thereof, composition containing it, time of administration, route of administration, duration of treatment, its potency, its rate of clearance and whether or not another drug is co-administered. The amount of ABT-869 Hydrate Crystalline Form 1 used to make a formulation to be administered daily to a patient in a single dose or in divided doses is from about 0.03 to about 200 mg/kg body weight. Single dose formulations contain these amounts or a combination of submultiples thereof.

ABT-869 Hydrate Crystalline Form 1 may be administered with or without an excipient, typically with an excipient. Excipients include but are not limited to, for example, encapsulating materials and additives such as absorption accelerators, antioxidants, binders, buffers, carriers, coating agents, coloring agents, diluents, disintegrating agents, emulsifiers, extenders, fillers, flavoring agents, glidants, humectants, lubricants, perfumes, preservatives, propellants, releasing agents, sterilizing agents, sweeteners, solubilizers, wetting agents, mixtures thereof and the like.

Excipients for preparation of formulations comprising or made with ABT-869 Hydrate Crystalline Form 1 to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, copovidone, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, povidone, peanut oil, potassium phosphate salts, potato starch, povidone, propylene glycol, Ringer's solution, safflower oil, sesame oil, silicon dioxide, sodium carboxymethyl cellulose, sodium phosphate salts, sodium lauryl sulfate, sodium sorbitol, sodium stearylfumarate, soybean oil, stearic acids, stearyl fumarate, sucrose, surfactants, talc, tragacanth, tetrahydrofurfuryl alcohol, triglycerides, vitamin E and derivatives thereof, water, mixtures thereof and the like.

Excipients for preparation of formulations comprising or made with ABT-869 Hydrate Crystalline Form 1 to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like.

Excipients for preparation of formulations comprising or made with ABT-869 Hydrate Crystalline Form 1 to be administered osmotically include, for example, chlorofluorohydrocarbons, ethanol, water, mixtures thereof and the like.

Excipients for preparation of formulations comprising or made with ABT-869 Hydrate Crystalline Form 1 to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like.

Excipients for preparation of formulations comprising or made with ABT-869 Hydrate Crystalline Form 1 to be administered rectally or vaginally include, but are not limited to, cocoa butter, polyethylene glycol, wax, mixtures thereof and the like.

Excipients for a tablet formulation made with ABT-869 Hydrate Crystalline Form 1 (10.0 mg) to be administered orally are Type K 28 Copovidone (conforms to NF and Ph. Eur. monograph specifications, 159.0 mg), Propylene Glycol Monolaurate (type 1) (conforms to Ph. Eur. Monograph specifications, 20.0 mg), Vitamin E prepared by esterifying d-alpha-tocopheryl acid succinate with polyethylene glycol 1000) (conforms to NF monograph specifications, 10 mg), mannitol (conforms to USP and Ph. Eur. monograph specifications, 194.0 mg), sodium stearylfumarate (conforms to USP and Ph. Eur. monograph specifications, 2.0 mg) and silicon dioxide (conforms to NF and Ph. Eur. monograph specifications, 5.0 mg).

ABT-869 Hydrate Crystalline Form 1 is also useful when administered with anticancer drugs such as alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, intercalating antibiotics, other kinase inhibitors, including other PTKs, mammalian target of rapamycin inhibitors, mitogen-activated extracellular signal-regulated kinase inhibitors, non-steroidal anti-inflammatory drugs (NSAIDs), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FC1, PU-3, radicicol, SNX-2112, STA-9090 VER49009 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam) ibuprofen cream, ALEVE® and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarubicin, pixantrone, rubitecan, sobuzoxane, SN-38, tafluposide, topotecan and the like.

Antibodies include AVASTIN (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON (toremifene), FASLODEX® (fulvestrant), FMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON® (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS (histrelin implant), VETORYL®, (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE (docetaxel), PNU100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachytherapy and sealed and unsealed source radiotherapy.

Additionally, ABT-869 Hydrate Crystalline Form 1 may be combined with other chemotherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotene), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN (hydroxydoxorubicin); O: Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906, GARDASIL® (quadrivalent human papillomavirus (Types 6, 11, 16, 18) recombinant vaccine), GASTRIMMUNE™ (gastrin-diptheria conjugate), GENASENSE™ (oblimersen sodium), GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafamib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), Taxoprexin® (DHA-paclitaxel), TELCYTA™ (TLK286), temilifene, TEMODAR® (temozolomide), tesmilifene, thalidomide, THER- ATOPE® (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel, poliglumex), YONDELIS™ (trabectedin), ZD-6126, ZINECARD® (dexrazoxane), zometa (zolendronic acid), zorubicin and the like.

It is also expected that ABT-869 Hydrate Crystalline Form 1 would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Preparation of ABT-869 and its utility as a PTK inhibitor is described in commonly-owned U.S. Pat. No. 7,297,709.

The following examples are presented to provide what is believed to be the most useful and readily understood description of procedures and conceptual aspects of this invention.

EXAMPLE 1

Preparation of ABT-869.¼ Ethanolate Crystalline Form 1

A mixture of ABT-869 hydrochloride in ethyl acetate and ethanol, in which the ABT-869 hydrochloride was completely soluble, was mixed with dibasic sodium phosphate. The organic layer was separated, treated with decolorizing carbon, and filtered. A small quantity of L-ascorbic acid was added, and the solution was concentrated. The ethyl acetate was removed by azeotropic distillation with ethanol. Additional ethanol may be added and the solution heated to dissolve any solid that forms. The solution was cooled to 25° C. and diluted with water, causing ABT-869.¼ Ethanolate Crystalline Form 1 to crystallize. The product was isolated, washed with water, and dried under reduced pressure, while monitoring residual ethyl acetate and ethanol (by gas chromatography (GC)) and water (by Karl Fischer (KF)). A yield of 92% is typical.

EXAMPLE 2

Preparation of ABT-869 Hydrate Crystalline Form 1

Following the neutralization with dibasic sodium phosphate, decolorizing carbon treatment and the removal of ethyl acetate as described in EXAMPLE 1, the mixture of ABT-869 in ethanol was gradually mixed with water at 25° C., with vigorous agitation. ABT-869.H$_2$O Crystalline Form 1 was isolated, washed with water, and dried under reduced pressure while monitoring residual ethyl acetate and ethanol (by GC) and water (by KF). The dried material may be delumped/milled to control particle size. A yield of 76% is typical.

EXAMPLE 3

Alternative Method to Prepare ABT-869 Hydrate Crystalline Form 1

This process was modified from the current process by adding a cosolvent to reduce the volume of the crystallization process.

Currently, the process uses a solution of ABT-869 dissolved in ethanol. This solution is slowly added to water. The current process requires a final volume of ~220 ml solvent/g ABT-869.

By adding acetic acid to the ethanol/ABT-869 solution, a more concentrated solution of ABT-869 can be made, reducing the final solvent volume to 60-80 ml solvent/g ABT-869. Because of equipment constraints, the more concentrated solution of ABT-869 allows for better mixing as well which helps to ensure the desired crystal formation.

100 g of ABT-869 was dissolved in a mixture of 590 g ethanol (200 proof) and 771 g of glacial acetic acid. 575 mg of ascorbic acid was added to avoid degradation of the product. The solution was stirred until all the solids dissolve. (If necessary, slight heating (not more than 30° C. for 30 min) can be used to assist dissolution.) The solution was cooled to 25° C.

4430 g of water was added to a glass lined jacketed reactor fitted with a retreat curve impeller. (Additional baffling can be used to help mixing efficiency.) The reactor was fitted with an addition tube with an outlet located above the surface of the liquid. The addition tube was situated so liquid will freely fall to the surface of the water (and not drip down the sides of the reactor or the shaft of the impeller). The tip of the addition tube should not be subsurface at any point during the addition. Reactor temperature was maintained at 25° C.+/−5° C.

A diaphragm pump or syringe pump was used to slowly add the solution of ABT-869 to the reactor. The solution was added through an inline filter to prevent addition of undissolved solids. The addition was completed at a constant addition rate over the course of not less than two hours. (It is critical that the agitation in the reactor be high (>500 rpm in a 250 ml to be safe) reactor. If the agitation is too low or the rate of addition is too high it is possible to nucleate a different crystal form.)

White solid appeared as soon as the ABT-869 solution contacts the water. Through the course of addition, the slurry thickens During the addition, samples can be taken to check the crystal form by x-ray.

To ensure desupersaturation, the mixture was stirred for not less than 1 hr. Samples can be taken to ensure the concentration in the liquors is correct.

The mixture was filtered through a pot filter fitted with a <10 μm pore size filter cloth (or filter paper). Some breakthrough of the solid occurred initially. After approximately one third of the sample is filtered, the liquors were recirculated to recover any solid that passed through the filter.

After filtration, the wetcake was washed with water (three times w/75 ml).

Typical yield at the lab scale in this process is >94%.

The solid was dried at 50° C. for NLT 12 hrs.

Final water content was <5.0 wt %. Final acetic acid content was <0.05 wt %. Crystal form was confirmed by x-ray and DSC.

Different solvents (or solvent mixtures) can be used to make the ABT-896 solution, including ethanol, N-methylpyrrolidone (NMP), dimethylformamide (DMF), ethanol/NMP, ethanol/acetic acid, ethanol/ethyl acetate, and ethanol/DMF, as are commercially available through Sigma Aldrich. Suitable solvents used in the process are any that do not phase separate with water and does not degrade ABT-869. Depending on the solvent used, the amount of water used in the process may have to be adjusted. Currently the process requires that the final solvent composition be >75% water in order to ensure that the correct crystal form be nucleated.

This process started with a solid ABT-869 sample. If ABT-869 is coming from a solution, then a solvent switch into ethanol/acetic acid is necessary.

Powder X-ray diffraction (PXRD) analysis of samples was conducted in the following manner. Samples were prepared by spreading the sample powder in a thin layer on an aluminum sample holder and gently flattening the sample with a microscope slide. Diffraction patterns were collected at ambient temperature and environmental conditions using an Inel G3000 diffractometer equipped with an incident beam germanium monochromator to provide Cu—$K_{\alpha_1}$ radiation. The X-ray generator was operated at a voltage of 40 kV and a current of 30 mA. The Inel G3000 is equipped with a position sensitive detector that monitors all diffraction data simultaneously. The detector was calibrated by collecting the attenuated direct beam for seven seconds in 1 degree intervals across a 90 degree two theta range. The calibration was checked against a silicon line position reference standard (NIST 640c).

FIG. 1 is a powder x-ray diffraction pattern for N-[4-(3-amino-1H-indazol-4-yl)phenyl]-N'-(2-fluoro-5-methylphenyl)urea Hydrate Crystalline Form 1, showing 2 theta values.

It is meant to be understood that relative intensities of peak heights and/or peak positions in a PXRD pattern may vary and will be dependent on variables such as the temperature, size of crystal size or morphology, sample preparation, or sample height in the analysis well of the X-ray diffractometer.

It is also meant to be understood that peak positions may vary when measured with different radiation sources. For example, Cu—$K\alpha_1$, Mo—$K\alpha$, Co—$K\alpha$ and Fe—$K\alpha$ radiation, having wavelengths of 1.54060 Å, 0.7107 Å, 1.7902 Å and 1.9373 Å, respectively, may provide peak positions which differ from those measured with Cu—$K\alpha$ radiation, which has a wavelength of 1.5478 Å.

The term "about" preceding a series of peak positions means that all of the peaks of the group which it precedes are reported in terms of angular positions (two theta) with an allowable variability of ±0.1° as specified by the U.S. Pharmacopeia, pages 1843-1884 (1995). The variability of ±0.1° is intended to be used when comparing two powder X-ray diffraction patterns. In practice, if a diffraction pattern peak from one pattern is assigned a range of angular positions (two theta) which is the measured peak position ±0.1° and if those ranges of peak positions overlap, then the two peaks are considered to have the same angular position. For example, if a peak from one pattern is determined to have a position of 11.0°, for comparison purposes the allowable variability allows the peak to be assigned a position in the range of 10.9.°-11.1°.

Accordingly, for example, the phrase "about 6.2°, 12.0°, 12.4°, 12.8°, 13.4°, 14.2°, 15.2°, 15.6°, 16.2° and 19.7°," as used herein, means about 6.2°, about 12.0°, about 12.4°, about 12.8°, about 13.4°, about 14.2°, about 15.2°, about 15.6°, about 16.2° and about 19.7, which, in turn, means 6.2°±0.1°, 12.0°±0.1°, 12.4°±0.1°, 12.8°±0.1°, 13.4°±0.1°, 14.2°±0.1°, 15.2°±0.1°, 15.6°±0.1°, 16.2°±0.1° and 19.7°±0.1°.

The term "about" preceding a temperature means the given temperature ±2° C. For example, about 25° C. means 25° C.±2° C. or 23° C.-27° C.

Heat flow was measured using a differential scanning calorimeter (model 2920 with Thermal Advantage version 1. 1A operating software (TA Instruments, New Castle, Del.). A sample (1-4 mg) was weighed into an aluminum pan, and the pan was covered with and aluminum lid containing a pinhole to allow vapor to escape. The partially sealed pan was placed in the furnace and heated in an open pan at a rate of 10° C./min. Indium standards were used for temperature and heat of fusion calibration. Data analysis was performed using separate software (Universal Analysis for Windows 2000/XP, version 4.2E, TA Instruments, New Castle, Del.).

Thermogravimetric analysis (TGA) data show that the solid loses 2.9% weight below 70° C. The weight loss from the solid corresponds to a broad endotherm in the differential scanning calorimetry (DSC) thermogram. The solid has an apparent melting endotherm with an extrapolated onset of 182.1° C.

The foregoing is meant to be illustrative of the invention and not intended to limit it to the disclosed embodiments. Variations and changes obvious to one skilled in the art are intended to be within the scope and nature of the invention as defined in the claims.

We claim:

1. N-[4-(3-Amino-1H-indazol-4-yl)phenyl]-N'-(2-fluoro-5-methylphenyl)urea Hydrate Crystalline Form 1 which, when measured at about 25° C. with radiation at 1.54178 Å, is characterized by a powder diffraction pattern having respective 2θ values of about 6.2°, 12.0°, 12.4°, 12.8°, 13.4°, 14.2°, 15.2°, 15.6°, 16.2° and 19.7°.

* * * * *

UNITED STATES PATENT AND TRADEMARK OFFICE
CERTIFICATE OF CORRECTION

| | | |
|---|---|---|
| PATENT NO. | : 7,947,843 B2 | Page 1 of 1 |
| APPLICATION NO. | : 12/251879 | |
| DATED | : May 24, 2011 | |
| INVENTOR(S) | : Thomas B. Borchardt | |

It is certified that error appears in the above-identified patent and that said Letters Patent is hereby corrected as shown below:

Column 1, Line 44 "tive 2O values" should read as --tive 2θ values--

Column 7, Line 28 "FMARA®" should read as --FEMARA®--

Column 7, Line 31 "NILANDRON®" should read as --NILANDRON™--

Signed and Sealed this
Eighteenth Day of December, 2012

David J. Kappos
*Director of the United States Patent and Trademark Office*